(12) United States Patent
Cabiac et al.

(10) Patent No.: US 10,099,205 B2
(45) Date of Patent: Oct. 16, 2018

(54) CATALYST COMPRISING PALLADIUM AND SILVER, AND ITS APPLICATION FOR SELECTIVE HYDROGENATION

(71) Applicant: IFP Energies Nouvelles, Rueil-Malmaison (FR)

(72) Inventors: Amandine Cabiac, Givors (FR); Vincent Zozaya, Saint-Symphorien-D'ozon (FR); Alexandre Chambard, Javerlhac (FR); Cecile Thomazeau, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/370,705

(22) Filed: Dec. 6, 2016

(65) Prior Publication Data

US 2017/0095797 A1   Apr. 6, 2017

Related U.S. Application Data

(62) Division of application No. 13/906,567, filed on May 31, 2013, now abandoned.

(30) Foreign Application Priority Data

Mar. 31, 2012   (FR) ..................................... 12 01572

(51) Int. Cl.

| | |
|---|---|
| *B01J 37/16* | (2006.01) |
| *B01J 23/50* | (2006.01) |
| *B01J 35/00* | (2006.01) |
| *B01J 35/10* | (2006.01) |
| *B01J 37/02* | (2006.01) |
| *B01J 37/08* | (2006.01) |
| *B01J 37/00* | (2006.01) |

(52) U.S. Cl.
CPC ........... *B01J 23/50* (2013.01); *B01J 35/0006* (2013.01); *B01J 35/1014* (2013.01); *B01J 35/1019* (2013.01); *B01J 37/009* (2013.01); *B01J 37/024* (2013.01); *B01J 37/0236* (2013.01); *B01J 37/08* (2013.01); *B01J 37/16* (2013.01)

(58) Field of Classification Search
None
See application file for complete search history.

(56) References Cited

U.S. PATENT DOCUMENTS

| | | | | |
|---|---|---|---|---|
| 4,484,015 A | * | 11/1984 | Johnson | B01J 23/50 585/259 |
| 5,583,274 A | * | 12/1996 | Cheung | C07C 5/09 585/258 |
| 6,054,409 A | * | 4/2000 | Nguyen Thanh | B01J 23/44 502/328 |
| 7,932,205 B2 | | 4/2011 | Coupard et al. | |
| 8,178,735 B2 | | 5/2012 | Coupard et al. | |
| 2007/0191651 A1 | * | 8/2007 | Coupard | B01J 23/62 568/959 |
| 2010/0197488 A1 | | 8/2010 | Hagemeyer et al. | |
| 2010/0236986 A1 | * | 9/2010 | Fischer | B01J 23/58 208/138 |
| 2011/0201857 A1 | | 8/2011 | Coupard et al. | |

FOREIGN PATENT DOCUMENTS

| | | | |
|---|---|---|---|
| EP | 0780155 | | 6/1997 |
| FR | 2720956 | | 12/1995 |
| FR | 2882531 | | 9/2006 |
| FR | 2922784 | * | 1/2009 |
| FR | 2963344 | | 2/2012 |

OTHER PUBLICATIONS

Search Report for FR-1201571 dated Dec. 4, 2012.
Institut Francais du Petrole, "Hydrogenation catalyust for selective hydrogenation for e.g. acetylene," Espacenet, Publication Date: Dec. 15, 1995; English Abstract of FR-2720956.
Institut Francais du Petrole, "Selective hydrogenation catalyst and process using this catalyst," Espacenet, Publication Date: Jun. 25, 1997; English Abstract of EP-0780155.
IFP Energies Nouvelles, "Method for selective hydrogenation in the presence of a catalyst of a group VII metal prepared by at least one oligosaccharide cyclic," Espacenet, Publication Date: Feb. 3, 2012; English Abstract of FR-2963344.

* cited by examiner

*Primary Examiner* — Melvin C. Mayes
*Assistant Examiner* — Colette B Nguyen
(74) *Attorney, Agent, or Firm* — Millen White Zelano and Branigan, PC; Csaba Henter

(57) ABSTRACT

Disclosed are a catalyst, its preparation and use in selective hydrogenation, which catalyst has a porous support grain on which are deposited palladium and silver, and at least one alkali and/or alkaline earth metal; the porous support contains a refractory silica, alumina and/or silica-alumina oxide, where at least 80 wt. % of the palladium is distributed in a crust at the periphery of the support, and at least 80 wt. % of the silver is distributed in a crust at the periphery of the support, the local content of palladium at each point along the diameter of the grain follows the same course as the local content of silver.

11 Claims, 1 Drawing Sheet

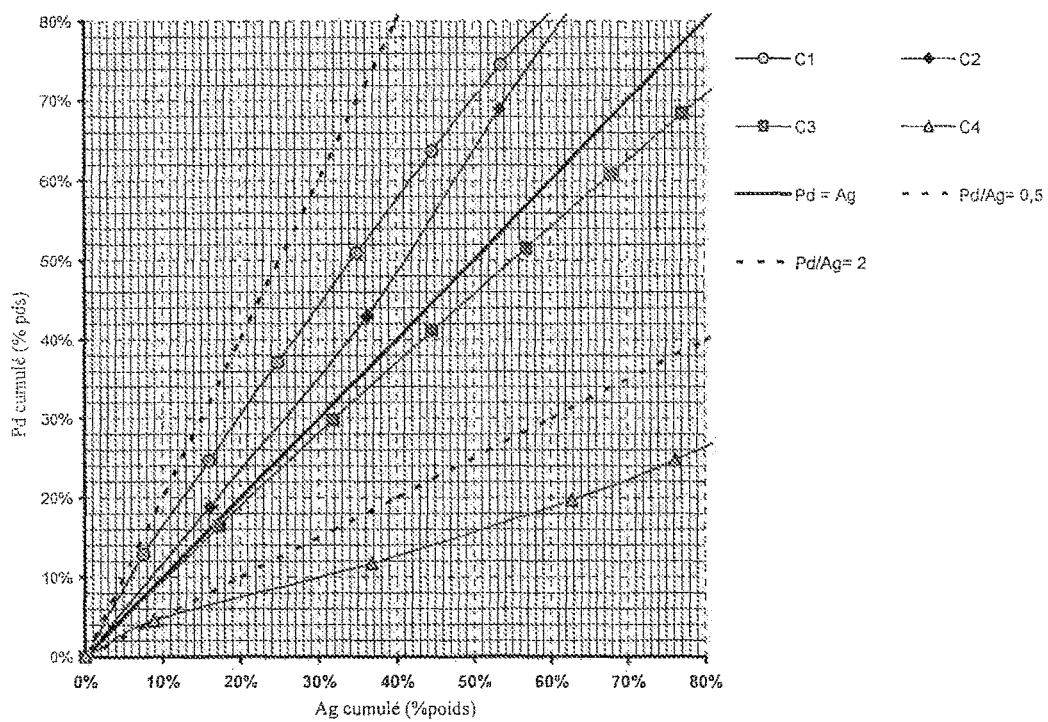

CATALYST COMPRISING PALLADIUM AND SILVER, AND ITS APPLICATION FOR SELECTIVE HYDROGENATION

The process of selective hydrogenation allows the polyunsaturated compounds in oil cuts to be transformed by conversion of the most unsaturated compounds into the corresponding alkenes while avoiding total saturation and thus the formation of the corresponding alkanes.

The object of the invention is to propose a catalyst and a method for preparing the said catalyst. This catalyst performs very well in processes of selective hydrogenation of the unsaturated hydrocarbon compounds present in hydrocarbon cuts, preferably cuts derived by steam cracking and/or catalytic cracking, and in particular from C3 cuts.

PRIOR ART

The catalysts of selective hydrogenation of these cuts are often palladium-based, in the form of small particles of metal deposited on a support which may be a refractory oxide in the form of beads, extrudates or trilobes, or forms having other geometries. The palladium content and the size of the particles of palladium are among the criteria that are important for catalyst activity and selectivity.

The macroscopic distribution of the particles of metal in the support is also an important criterion, principally within the context of rapid, sequential operations, such as selective hydrogenation. In order to avoid the problems of intragranular material transfer that can lead to lack of activity and a loss of selectivity, it is generally necessary for these elements to be located within a crust at the periphery of the support.

Thus, FR 2 922 784 describes a supported catalyst comprising a crust formed of particles of palladium with a homogeneous palladium particle size distribution within the range 2 to 6 nm. These catalysts have dispersions of palladium within the range 25 to 70% and palladium particle densities within the range 1500 to 4100 particles of palladium per $\mu m^2$ (denoted $Pd/m^2$). They further comprise an alkaline or alkaline-earth compound homogeneously distributed within the support grain. This patent similarly describes a method of preparing this catalyst by colloidal suspension of palladium.

Within the context of hydrogenation of light cuts, the addition of at least one second metal, preferably a group IB metal preferably selected from Ag, Au, Cu, highly preferably Ag, enables the selectivity to be improved.

These bimetallic effects are generally linked to the interaction created between the two elements. It thus appears that the identification of a plurimetallic catalytic system is conditional upon establishing this interaction.

Indeed, it is known to the person skilled in the art that, for the reactions of hydrogenation of polyunsaturated molecules such as the diolefins or the acetylenes, the rate of reaction depends on the size of the metallic particles, this result generally being described by the term "structural sensitivity". A peak is generally observed for a size of the order of 3 to 4 nm, this value being variable as a function notably of the molecular mass of the reactants (described in M. Boudart, W. C. Cheng, J. Catal. 106, 1987, 134, and S. Hub, L. Hilaire, R. Touroude, Appl. Catal. 36, 1992, 307). It is thus important to obtain a particle size distribution centred on the optimal value, as well as a minimum distribution around this value.

The identification of bimetallic couples has been the object of much research in the field of selective hydrogenation reactions (in the work V. Ponec, G. C. Bond, Catalysis by Metal and Alloys, Elsevier, Amsterdam, 1995). These studies further revealed the difficulty in obtaining the desired synergistic effect, this effect being conditional upon the method of synthesis selected. Thus, the local composition of the active phase plays a key role in achieving elevated catalytic performances. As the yields obtained are the result of transformations exerted upon each particle, the composition of said particles must be adapted to the optimal formulation and the particles must be homogeneous with one another.

Finally, the macroscopic distribution of the elements in the support beads similarly constitutes an important criterion. It is preferable to deposit the elements in a fine crust at the periphery of the support grains.

Thus, FR 2 882 531 describes a bimetallic catalyst for which the size, composition and distribution of the bimetallic particles within the support beads are adapted to the requirements of the selective hydrogenation reactions. The characteristics of the catalyst are notably obtained by a particular process of preparation comprising, not a conventional impregnation method, but the use of impregnation by colloidal suspension. More particularly, the preparation process comprises preparing a colloidal suspension of an oxide of a first metal M1, placing a second metal M2 in contact in a second step, and placing this in contact with the support in a third step, drying and then optional calcination.

US2010/217052 describes a supported PdAg catalyst, in which the palladium and the silver partially form an alloy in a thin peripheral crust, enabling catalysts to be obtained that are particularly suitable for selective hydrogenation of C2 cuts. The proportion of particles forming an alloy is measured by adsorption of CO onto the catalytic surface. The support used is of a very small surface area (1 to 80 $m^2/g$). The preparation process comprises a step of impregnation of the two metals into a solution containing water and an organic solvent miscible in the water, optional drying, and calcination at a maximum temperature of 400° C. The percentage of water in the impregnation solution allows variation of the thickness of the palladium and silver crust.

The aim of the present invention is to obtain catalysts having very good performances for the processes of selective hydrogenation of unsaturated hydrocarbon compounds present in the hydrocarbon cuts derived by steam cracking and/or catalytic cracking, and in particular in the C3 cuts.

The Applicants discovered—and this constitutes the subject of the present invention—that the performances of a bimetallic PdAg crust catalyst could be distinctly improved when the atoms of silver are in close proximity to the palladium atoms within the crust containing the two metals. This is because the thin crust of the catalyst thus comprises palladium and silver arranged in a specific way: the local content of palladium at each point along the diameter of the grain follows the same course as the local content of silver. In other words, when the local content of palladium at a given point along the diameter increases relative to another given point along the diameter, the silver content similarly increases. The highest content of palladium and of silver is generally observed to be found close to the surface of the support grain and to decrease gradually towards the interior of the grain. This course of the contents of palladium and silver may be expressed by a Proximity Ratio PR, which will be defined below.

The close proximity, which is linked to other parameters, such as the specific surface area of the support, enables catalysts that are particularly suited to selective hydrogenation reactions to be obtained.

This particular proximity of palladium and silver on the support is due to the preparation process. This preparation process in fact comprises two very distinct steps, a first step wherein the palladium is deposited by a colloidal method followed by calcination, and a second step wherein the silver is deposited on the catalyst containing the palladium having previously undergone liquid phase reduction. The colloidal suspension technique yields very thin crusts with homogeneous metallic particle sizes. The preparation process also enables the use of supports having fairly large specific surface areas, notably for preference between 65 and 150 m²/g. This allows better fixation of the metal particles on the support and minimises sintering during calcination performed at high temperature (above 450° C.). A heat treatment between 450° C. and 700° C. improves the proximity ratio PR between the atoms of palladium and those of silver, enabling catalysts which perform better in selective hydrogenation to be obtained.

The invention thus also relates to the preparation of the catalyst and its use in selective hydrogenation.

DETAILED DESCRIPTION OF THE INVENTION

Characteristics of the Catalyst

The present invention relates to a catalyst comprising a porous support grain on which is deposited palladium and silver and at least one metal selected from the group consisting of the alkalis and alkaline earths, the porous support comprising at least one refractory oxide selected from the group consisting of silica, alumina and silica-alumina, the specific surface area of the porous support being within the range 10 to 150 m²/g, the palladium content of the catalyst being within the range 0.05 to 0.6 wt. %, the silver content of the catalyst being within the range 0.02 to 3 wt. %, at least 80 wt. % of the palladium being distributed in a crust at the periphery of the support, the thickness of the said crust being within the range 10 to 160 µm, at least 80 wt. % of the silver being distributed in a crust at the periphery of the support, the thickness of the said crust being within the range 10 to 160 µm, the local content of palladium at each point along the diameter of the grain following the same course as the local content of silver, the sum of the contents of alkali and/or alkaline-earth metals being within the range 0.02 to 5 wt. %.

A catalyst is preferably used wherein the specific surface area of the said porous support is within the range 65 to 150 m²/g, wherein the content of palladium in the catalyst is within the range 0.05 to 0.4 wt. %, the silver content of the catalyst is within the range 0.05 to 0.3 wt. %, at least 80 wt. % of the palladium is distributed within a crust at the periphery of the support, the thickness of the said crust is within the range 10 to 110 µm, at least 80 wt. % of the silver is distributed within a crust at the periphery of the support, and the thickness of the said crust is within the range 10 to 110 µm.

According to the invention, the porous support grain is advantageously in the form of beads, trilobes, extrudates, pellets, or irregular, non-spherical agglomerates, the specific form of which may be the result of a crushing step. Highly advantageously, the said support is in the form of beads or extrudates. Yet more advantageously, the said support is in the form of beads.

The pore volume of the support is generally within the range 0.1 to 1.5 cm³/g, preferably within the range 0.3 to 1.3 cm³/g.

The porous support comprises at least one refractory oxide selected from the group consisting of silica, alumina and silica-alumina. Preferably, the support is alumina.

The alkali metal is generally selected from the group consisting of lithium, sodium, potassium, rubidium and caesium, preferably of lithium, sodium and potassium, highly preferably sodium and potassium. Still more preferably, the alkali metal is sodium.

The alkaline-earth metal is generally selected from the group consisting of magnesium, calcium, strontium and barium, preferably magnesium and calcium, and highly preferably magnesium.

The alkali metal, when present, is preferably homogeneously distributed through the support, with a coefficient R, hereinafter defined, within the range 0.8 to 1.2.

The alkaline-earth metal, when present, is preferably homogeneously distributed through the support with a coefficient R, hereinafter defined, within the range 0.8 to 1.2.

The catalyst of the present invention may be characterised by a plurality of parameters which will be described in what follows, notably:
- the coefficient R, which expresses the homogeneous distribution of the alkaline and/or alkaline-earth element through the support grain,
- the thickness of the crust,
- the proximity ratio PR, which expresses the proximity of the palladium atoms to the atoms of silver at a given point within the crust,
- the metallic dispersion, which enables deduction of the mean size of the particles of metal.

Coefficient R

The distribution profiles of the elements within the grains of catalysts are obtained using a Castaing microprobe. At least 30 analysis points are recorded along the diameter of the bead or of the extrudate—about 10 points on the crust of the active element, and about 10 points at the centre of the grain. Thus is obtained the distribution profile c(x) for x∈[−r; +r], where c is the local concentration of the element, r the radius of the bead or extrudate, and x the position of the analysis point along the diameter of the grain relative to the centre of this grain.

The distribution of the elements is characterised by a dimensionless coefficient R which weights the local concentration by a weight that increases as a function of the position on the diameter. By definition:

$$R = \int_{-r}^{r} c(x) x^2 \, dx \Big/ \frac{r^2}{3} \int_{-r}^{r} c(x) \, dx$$

Thus, an element with a uniform concentration has a coefficient R equal to 1, an element deposited in a dome profile (concentration at the core higher than the concentration at the edges of the support) has a coefficient of more than 1, and an element distributed in a crust profile (concentration at the edges higher than the concentration at the core of the support) has a coefficient of less than 1. The analysis by Castaing microprobe produces values for the concentrations for a finite number of values of x, and so R is evaluated numerically using integration methods which are well known to the person skilled in the art. Preferably, R is determined using the trapezium method.

The distribution of the alkali element is defined as being homogeneous when the distribution coefficient R as defined above is within the range 0.8 to 1.2.

The distribution of the alkaline-earth element is defined as being homogeneous when the distribution coefficient R as defined above is within the range 0.8 to 1.2.

Crust Thickness

When the palladium and silver are distributed as a crust, their local concentration generally decreases gradually when it is measured starting from the edge of the catalytic grain towards the interior. A distance from the edge of the grain, at which the local palladium and silver concentration becomes zero, can often not be determined accurately and reproducibly. In order to measure a crust thickness which is significant for the majority of palladium and silver particles, the crust thickness is defined as the distance to the edge of the grain containing 80% of the element.
Starting from the distribution profile obtained by Castaing microprobe, the cumulative quantity $Q(y)$ of the element in the grain is calculated as a function of the distance y to the edge of the grain.
For a bead:

$$Q(y) = \int_{-r}^{-y} c(x) 4\pi \cdot x^2 dx + \int_{y}^{r} c(x) 4\pi \cdot x^2 dx$$

For an extrudate:

$$Q(y) = \int_{-r}^{-y} c(x) 2\pi \cdot x dx + \int_{y}^{r} c(x) 2\pi \cdot x dx$$

$Q(r)$ thus corresponds to the total quantity of the element in the grain. The following equation is then solved numerically for y:

$$\frac{Q(y)}{Q(r)} = 0.8$$

where c is a strictly positive function; Q is thus a strictly increasing function, and this equation has a single solution which is the thickness of the crust.

Proximity Ratio PR

The PdAg catalysts are characterised by Castaing microprobe. This analysis enables the mass concentration of metal Pd, Ag to be ascertained locally.

For a catalyst, this analysis allows determination of the relative distribution of the two metals along the catalytic grain by integration of a succession of FX analyses at a distance y on the edge of the grain. The formula enabling the proximity of the two metals to be estimated is the following:

$$\text{Proximity ratio} = PR(y) = \frac{Q(y)Pd / Q(r)Pd}{Q(y)Ag / Q(r)Ag}$$

where:
Q (y) Pd=Sum of the palladium concentrations between the edge of the catalytic grain and a distance y from the edge of the grain (wt. %)
Q (y) Ag=Sum of the silver concentrations between the edge of the catalytic grain and a distance y from the edge of the grain (wt. %)
Q (r) Pd=Total palladium content of the catalytic grain (wt. %)
Q (r) Ag=Total silver content of the catalytic grain (wt. %).

Thus is defined a proximity criterion, which takes into account the relative locations of the two metals within the support. This parameter, which is determined by microprobe, represents the mass ratio at any point y on the support, of the added metallic elements, in our case Pd and Ag. The proximity ratio of a catalyst containing locally uniformly distributed metals will be 1.

In the catalyst according to the invention, the proximity ratio PR is within the range 0.5 to 2, preferably 0.8 to 1.4.

Metallic Dispersion D

The measurements of metallic dispersion are performed to determine the mean size of the particles of palladium. These measurements are performed after the first step of the process, wherein only the palladium is introduced onto the support.

The metallic dispersion measurements are carried out by chemisorption of carbon monoxide CO onto the catalyst which has previously been reduced in 1 liter of hydrogen per hour per gram of catalyst, with a temperature ramp-up of 300° C./h and a constant temperature stage of two hours at 150° C. The catalyst is then flushed for 1 hour at 150° C. in helium then cooled to 25° C. in helium.

CO chemisorption is carried out dynamically at 25° C. using the methods which are well known to the person skilled in the art, resulting in a volume of chemisorbed CO, from which the person skilled in the art can calculate the number of molecules of CO which have been chemisorbed.

A stoichiometric ratio of one molecule of CO per atom of Pd surface is assumed in order to calculate the number of atoms of surface Pd. The dispersion is expressed as the % of surface Pd atoms with respect to the total number of Pd atoms present in the catalyst sample.

The metallic dispersion D of palladium is generally within the range 10% to 70%, preferably 15% to 60%.

The mean crystallite size is deduced from these dispersion measurements by application of the dispersion-particle size relationships known to the person skilled in the art and described in "Analyse physico-chimique des catalyseurs industriels" [Physico-Chemical Analysis of Industrial Catalysts], Chapter I, Editions Technip, Paris, 2001.

The palladium particle size distribution of the catalyst is homogeneous, within the range 2 to 6 nm.

Following the introduction of the silver into the catalyst (second step), the metallic dispersion of palladium falls. We will therefore refer to this as the "apparent" dispersion, within the range 5 to 50%. However, the introduction of silver does not alter the particle size distribution of the catalyst, which remains within the range 2 to 6 nm.

Palladium Particle Density De

The catalyst may also be characterised by the palladium particle density De, as defined in FR2922784.

In the case of a bead of support with volume Vt and radius r wherein the palladium is present in the form of a crust of thickness e, the palladium particle density is obtained using the following formula:

$$De = \frac{(\% \, Pd) \cdot N_a}{S_{BET} \cdot M_{Pd} \cdot n_{Pd} \cdot 10^{14}} \frac{V_t}{V_c} \quad (1)$$

where:
De: density of particles (as the number of palladium particles per $\mu m^2$)
% Pd: quantity of Pd by weight (grams of Pd per 100 grams of catalyst)
$N_a$: Avogadro's number ($6.022 \times 10^{23}$ atoms/mole)
$S_{BET}$: specific surface area of support (in $m^2/g$)
$M_{Pd}$: molar mass of palladium (106.42 g/mole)
$n_{Pd}$: number of palladium atoms per palladium particle
$V_t$: total volume of support bead in $mm^3$
$V_t = 4/3 \cdot \pi \cdot r^3$ (r being the radius of the bead)
$V_c$: volume of crust in $mm^3$;
$V_c$: $V_t - 4/3 \cdot \pi \cdot (r-e)^3$ (e being the thickness of the crust).

The number of Pd atoms per metallic particle as a function of the particle size is determined using the Van Hardeveld and Hartog model (described in R Van Hardeveld, F Hartog, Surf Sci 15 (1969) 189).

The person skilled in the art may calculate the palladium particle density using a mathematical formula depending on the form of support under consideration. Thus, for a support the form of which is other than a bead, the density equation is still valid, but the formulae for calculating $V_t$ and $V_c$ must be adapted by the person skilled in the art as a function of the geometry of the support.

The density of palladium particles within the crust, denoted De, is advantageously within the range 1500 to 4100 particles of palladium per $\mu m^2$, preferably within the range 1550 to 4000 particles of palladium per $\mu m^2$, preferably [sic] 1600 to 3950 particles of palladium per $\mu m^2$.

Process for Preparing the Catalyst

The invention also relates to a process for preparing the catalyst, generally comprising the following steps:
a first step, referred to as step 1, wherein the palladium is deposited by a colloidal method, following by drying and calcination,
a second step, referred to as step 2, wherein the silver is deposited following liquid phase reduction of the catalyst containing palladium, followed by drying and calcination.

It is important to highlight that the preparation process is carried out in two distinct steps including an intermediate calcination step between the two metal-deposition steps. Thus, the palladium is first introduced via a colloidal pathway, then dried and calcined, after which the silver is introduced, preceded by a step of liquid phase reduction of the catalyst, then dried and calcined, preferably at high temperature.

More particularly, the process for preaparing the catalyst comprises:
a step wherein the palladium is introduced onto the support, referred to as step 1, comprising the following steps:
a step 1a) wherein, in an apparatus, a colloidal suspension of palladium oxide or palladium hydroxide is prepared in an aqueous phase by mixing an aqueous solution 1 comprising at least one hydroxide selected from the group consisting of alkali hydroxides and alkaline-earth hydroxides and an aqueous solution 2 comprising at least one palladium precursor, the solution 2 then the solution 1 being poured into the apparatus or solutions 1 and 2 being poured simultaneously into the apparatus,
a step 1b) wherein the said colloidal suspension is impregnated onto a porous support grain having a specific surface area within the range 10 to 150 $m^2/g$,
a step 1c) wherein the said impregnated support obtained in step 1b) is matured,
a step 1d) wherein the catalyst obtained in step 1c) is dried,
a step 1e) wherein the catalyst obtained in step 1d) is calcined,
then a step wherein the silver is introduced, referred to as step 2, comprising the following steps:
a step 2a), wherein the catalyst prepared in accordance with step 1 is reduced by placing it in contact with an aqueous solution comprising at least one liquid phase reducing agent,
a step 2b), wherein the catalyst obtained in step 2a) is filtered,
a step 2c), wherein the catalyst prepared in step 2b) is impregnated by placing it in contact, under agitation, with an aqueous solution comprising a silver precursor salt,
a step 2d), wherein the catalyst obtained in step 2c) is filtered,
a step 2e), wherein the catalyst obtained in step 2d) is dried,
a step 2f), wherein the catalyst obtained in step 2e) is calcined, preferably at 450° C. to 700° C.

The different steps 1 and 2 are described in detail in what follows.

Step 1: Deposition of Palladium Using a Colloidal Method

Step 1a) Preparation of a Colloidal Suspension of Palladium

The colloidal suspension is generally obtained by hydrolysis of the palladium cation in an aqueous medium, which results in the formation of particles of palladium oxides or hydroxides in suspension.

The aqueous solution of alkali hydroxides or alkaline-earth hydroxides is generally selected from the group consisting of aqueous solutions of sodium hydroxide and aqueous solutions of magnesium hydroxide. Preferably, a solution of potassium hydroxide is used, yet more preferably an aqueous solution of sodium hydroxide.

The palladium precursor is generally selected from the group consisting of palladium chloride, palladium nitrate, and palladium sulphate. Highly preferably, the palladium precursor salt is palladium nitrate.

The aqueous solution 2 comprising at least one palladium precursor salt then the aqueous solution 1 comprising at least one alkali or alkaline-earth hydroxide are generally poured into the apparatus. Solutions 1 and 2 may be poured simultaneously into the apparatus. Preferably, the aqueous solution 2 then the aqueous solution 1 are poured into the apparatus.

The colloidal suspension generally remains in the apparatus for a residence time within the range 0 to 20 hours. The pH of the colloidal suspension may be modified during this residence time by adding quantities of acid or base which are compatible with the stability of the colloidal suspension.

In general, the preparation temperature is within the range 5° C. to 40° C., and preferably within the range 15° C. to 35° C. The concentration of palladium is preferably within the range 2 to 100 mmol per liter, more preferably within the range 4 to 50 mmol per liter.

The concentrations of solutions 1 and 2 are generally selected so as to obtain a pH of the colloidal suspension within the range pH=1.0 to pH=3.5.

Step 1b) Deposition of the Colloidal Suspension by Impregnation onto a Support

The colloidal suspension prepared in step 1a) is then impregnated onto a support.

The support may optionally undergo a set of treatments prior to the impregnation step, such as calcining or hydration steps. The support may also already comprise one or more metallic elements prior to impregnation of the colloidal suspension. Metallic elements may also be introduced into the colloidal suspension. These metallic elements may be introduced either using conventional techniques or using the process of the present invention.

The colloidal suspension is preferably poured onto the support. The volume of the colloidal suspension is generally within the range 0.9 to 1.1 times the pore volume of the support.

This process may be carried out either discontinuously, i.e. the step for preparing the colloidal suspension precedes the step for impregnation onto the support, and the essential part of the colloidal suspension is sent all at once to the impregnation step, or continuously, i.e. the product obtained in step 1a) is sent continuously after adjusting the residence time for the colloidal suspension in step 1b).

An example of a continuous process which may be cited is a process wherein solutions 1 and 2 are poured simultaneously into a tank which continuously overflows into a zone comprising the support to be impregnated.

Step 1c) Maturation

After impregnation, the impregnated support is generally matured in the moist state preferably for 0.5 to 40 h, highly preferably for 1 to 30 h.

Step 1d) Drying

The catalyst precursor is generally dried in order to eliminate all or a portion of the water introduced during impregnation, preferably at a temperature within the range 50° C. to 250° C., more preferably 70° C. to 200° C. The duration of drying is generally within the range 0.5 h to 20 h.

Drying is generally carried out in air or in air from the combustion of a hydrocarbon, preferably methane. The cited streams of air may contain 0 to 80 grams of water per kg of air, with oxygen within the range 5 to 25 vol. % and carbon dioxide within the range 0 to 10 vol. %.

Step 1e) Calcining

After drying, the catalyst is calcined, generally in air, or in air from the combustion of a hydrocarbon, preferably methane. The cited streams of air may contain 0 to 80 grams of water per kg of air, oxygen within the range 5 to 25 vol. % by volume and carbon dioxide within the range 0 to 10 vol. %. The calcining temperature is generally within the range 250° C. to 900° C., preferably within the range from approximately 300° C. to approximately 500° C. The duration of calcining is generally within the range 0.5 h to 5 h.

According to a first variant of this step 1 of the process, the pH, the residence time of the colloidal suspension and the specific surface area of the support are fixed within their respective ranges. The palladium content, within the range 0.05 to 0.6 wt. %, is then adjusted in order to obtain a palladium particle density in the crust within the range 1500 to 4100 particles of palladium per $\mu m^2$.

According to a second variant of this step 1 of the process, the palladium content, within the range 0.05 to 0.6 wt. %, the residence time of the colloidal suspension and the specific surface area of the support are fixed within their respective ranges. The pH is then adjusted in order to obtain a palladium particle density in the crust within the range 1500 to 4100 particles of palladium per $\mu m^2$.

Following this step 1, a supported catalyst precursor is obtained, comprising a crust formed by particles of palladium having a homogeneous palladium particle size distribution within the range 2 to 6 nm, as described in FR2922784. These catalysts have palladium dispersions within the range 25 to 70% and palladium particle densities within the range 1500 to 4100 palladium particles per $\mu m^2$ (denoted Pd/$\mu m^2$). They further comprise an alkali or alkaline-earth compound distributed homogeneously within the support grain.

Step 2: Deposition of Silver Following Reduction of the Catalyst

Step 2a) Reduction of the Catalyst Prepared in Step 1

The catalyst prepared in step 1 is then reduced in the liquid phase. The volume of the aqueous solution for reduction of the catalyst prepared according to step 1 is generally within the range 1 to 20 times the volume of the catalyst engaged.

The reducing agent used is selected from formic acid, citric acid, ascorbic acid, oxalic acid, sodium formiate, sodium acetate, sodium borohydride, formaldehyde, dextrose, hydrazine, hydrogen, or any other conventional liquid-phase reducer. The reducing agent/palladium molar ratio is preferably within the range 1 to 20, preferably 2 to 15.

The preparation temperature is preferably within the range 5 to 70° C., preferably 10 to 60° C.

The residence time of the said aqueous solution in the apparatus is within the range 0 to 20 h.

Preferably, the atmosphere is controlled, preferably with an inert or reducing gas. Highly preferably, an inert gas is used as the reaction atmosphere.

Step 2b) Filtration

The catalyst reduced in step 2a) is partially or totally filtered in accordance with the techniques known to the person skilled in the art. This aim of this step is to remove some or all of the reducing fluids.

Optionally, step 2b) may comprise one or more steps of washing of the solid, preferably with water, followed by the filtration step. The total volume of water engaged in the washing step(s) is within the range 1 to 30 times the volume of the engaged catalyst.

Step 2c) Deposition of Silver

The reduced, optionally washed, and filtered catalyst is placed in contact, under agitation, with an aqueous solution comprising the silver precursor in order to introduce silver into the catalyst.

The silver precursor is selected from the group consisting of silver nitrate, silver acetate, silver citrate, silver chloride, silver oxalate, or any other conventional silver precursor.

The volume of the aqueous solution of silver precursor is preferably within the range 1 to 20 times the volume of the engaged catalyst. The silver/palladium molar ratio is generally within the range 0.1 to 10, preferably 0.1 to 5, and highly preferably 0.2 to 2.

In general, the temperature of the solution is kept constant and is within the range 5° C. to 70° C. and preferably 10° C. to 60° C. The residence time of the said aqueous solution in the apparatus is preferably within the range 0.5 to 20 h.

The reaction atmosphere may be controlled, preferably with an inert or reducing gas. Highly preferably, if the atmosphere is controlled an inert gas is used as the reaction atmosphere.

Step 2d) Filtration

The catalyst prepared according to step 2c) is partially or totally filtered in accordance with all the techniques known to the person skilled in the art.

Optionally, step 2d) may comprise one or more step(s) of washing of the solid, preferably with water, followed by the filtration step. The total volume of water engaged for the washing step(s) is within the range 1 to 30 times the volume of the engaged catalyst.

Step 2e) Drying

The catalyst is generally dried to eliminate all or part of the water introduced during impregnation, preferably at a temperature within the range 50 to 250° C., more preferably 70° C. to 200° C. The duration of drying is preferably within the range 0.5 h to 20 h.

Drying is generally carried out in air or in air from the combustion of a hydrocarbon, preferably methane. The cited streams of air may contain 0 to 80 grams of water per kg of air, oxygen within the range 5 to 25 vol. % and carbon dioxide within the range 0 to 10 vol. %.

Step 2f) Calcining

After drying, the catalyst is calcined, generally in air, or in air from the combustion of a hydrocarbon, preferably methane. The cited streams of air may contain 0 to 80 grams of water per kg of air, oxygen within the range 5 to 25 vol. % and carbon dioxide within the range 0 to 10 vol. %.

The calcining temperature is generally within the range 450° C. to 900° C., preferably within the range from 450° C. to 700° C. The duration of calcining is generally within the range 0.5 h to 5 h.

Prior to use, the catalyst is generally activated by a treatment under a stream of hydrogen at a temperature between ambient temperature and approximately 500° C., preferably 80 to 180° C., and yet more preferably 100° C. to 160° C. This treatment may be performed in the reactor where the catalytic reaction will be performed (reduction in situ) or, as previously, in an independent apparatus (reduction off site, or ex situ).

The reduction is performed in the presence of a reducing gas comprising 25 vol % to 100 vol % hydrogen, preferably 100 vol. % hydrogen. The hydrogen is optionally made up with an inert gas for the reduction, preferably argon, nitrogen or methane.

The reduction generally comprises a temperature ramp-up phase followed by a constant-temperature stage.

The duration of the constant-temperature stage of the reduction is generally within the range 1 to 10 h, preferably 2 to 8 h.

The HSV is generally within the range 150 to 3000, preferably 300 to 1500 liters of reducing gas per h and per liter of catalyst.

The invention also relates to the catalyst capable of being obtained on the basis of the catalyst preparation process described in the present invention.

Use of the Catalyst According to the Invention

The catalyst of the invention may be used in reactions for hydrogenation of compounds comprising acetylenic, dienic, and olefinic functions.

The invention also relates to a process for selective hydrogenation by bringing a feed into contact with the catalyst according to the invention or with the catalyst prepared in accordance with the invention, said feed being selected from the group consisting of C3, C4 or C5 steam-cracking and/or catalytic-cracking cuts and steam cracking gasolines, also termed pyrolysis gasolines, the feeds preferably being C3 steam-cracking and/or catalytic-cracking cuts.

In accordance with a preferred application, the catalyst of the invention is employed for reactions for selective hydrogenation of polyunsaturated hydrocarbon cuts derived from steam cracking and/or from catalytic cracking, preferably polyunsaturated hydrocarbon cuts derived from steam cracking.

Processes for conversion of hydrocarbons such as steam cracking or catalytic cracking are operated at high temperature and produce a wide variety of unsaturated molecules such as ethylene, propylene, straight-chain butenes, isobutene, pentenes as well as unsaturated molecules containing up to approximately 15 atoms of carbon.

At the same time, polyunsaturated compounds are also formed: acetylene, propadiene and methylacetylene (or propyne), 1-2 and 1-3-butadiene, vinylacetylene and ethylacetylene, and other polyunsaturated compounds with a boiling point corresponding to the C5+ gasoline fraction.

All of these polyunsaturated compounds have to be eliminated in order to allow these various cuts to be used in petrochemical processes such as in polymerisation units.

The selective hydrogenation process has gradually imposed itself for eliminating polyunsaturated compounds from the C3 to C5 oil cuts and pyrolysis gasolines, as this process can convert the most unsaturated compounds into the corresponding alkenes, avoiding complete saturation and thus the formation of the corresponding alkanes.

Thus, for example, the C3 steam cracking cut may have the following mean composition: of the order of 90 wt. % propylene, of the order of 3% to 8 wt. % propadiene and methylacetylene, the remainder essentially being propane. In certain C3 cuts, between 0.1% and 2 wt. % of C2 and C4 may also be present. The specifications concerning the concentrations of these polyunsaturated compounds for petrochemicals and polymerisation units are very low: 20-30 ppm by weight MAPD (methylacetylene and propadiene) for chemical quality propylene and less than 10 ppm by weight or even up to 1 ppm by weight for "polymerisation" quality.

A C4 steam cracking cut has, for example, the following mean molar composition: 1% butane, 46.5% butene, 51% butadiene, 1.3% vinylacetylene (VAC) and 0.2% butyne. In certain C4 cuts, between 0.1% and 2 wt. % of C3 and C5 may also be present. Here again, the specifications are strict:

a diolefins content strictly below 10 ppm by weight for a C4 cut which will be used for petrochemicals or polymerisation.

A steam cracking C5 cut will, for example, have the following mean composition by weight: 21% pentanes, 45% pentenes, 34% pentadienes.

The pyrolysis gasoline corresponds to a cut with a boiling point which is generally within the range 0° C. to 250° C., preferably within the range 10° C. to 220° C. This feed generally comprises the C5-C12 cut with traces of C3, C4, C13, C14 and C15 (for example within the range 0.1% to 3 wt. % for each of these cuts). As an example, a C5-200° C. cut generally has the following composition in wt. %:

Paraffins: 8-12
Aromatics: 58-62
Monoolefins: 8-10
Diolefins: 18-22
Sulphur: 20-300 ppm Selective hydrogenation may be carried out in the gas or liquid phase, preferably in the liquid phase. A liquid phase reaction can in fact reduce the energy cost and increase the cycle time of the catalysts.

The selective hydrogenation is generally performed at a temperature within the range 0° C. to 500° C., a pressure within the range 0.1 to 20 MPa, an hourly space velocity (HSV) within the range 0.1 to 50 $h^{-1}$ for a liquid feed; and within the range 500 to 30000 $h^{-1}$ for a gaseous feed.

More particularly, in the case of selective hydrogenation of a C3 to C5 feed, and for a liquid phase reaction, the pressure is generally within the range 1 to 3 MPa, the temperature within the range 2° C. to 200° C. and the hydrogen/(polyunsaturated compounds to be hydrogenated) molar ratio within the range 0.1 to 10, preferably within the range 1 to 8. The hourly space velocity is within the range 1 to 200 $h^{-1}$.

In the case of selective hydrogenation of a C3 to C5 feed and for a gaseous phase hydrogenation reaction, the pressure is generally within the range 1 to 3 MPa, the temperature within the range 40° C. to 120° C. and the hydrogen/(polyunsaturated compounds to be hydrogenated) molar ratio within the range 0.1 to 4, preferably within the range 1 to 2. The hourly space velocity is within the range 1 to 15000 $h^{-1}$.

In the case of selective hydrogenation of pyrolysis gasoline, the hydrogen/(polyunsaturated compounds to be hydrogenated) molar ratio is generally within the range 1 to 2, the temperature is generally within the range 40° C. to 200° C., preferably within the range 50° C. to 180° C., the hourly space velocity (corresponding to the volume of hydrocarbon per volume of catalyst per hour) is generally within the range 0.5 $h^{-1}$ to 10 $h^{-1}$, preferably within the range 1 $h^{-1}$ to 5 $h^{-1}$, and the pressure is generally within the range 1.0 MPa to 6.5 MPa, preferably within the range 2.0 MPa to 3.5 MPa.

The hydrogen flow rate is adjusted in order to have available a sufficient quantity to theoretically hydrogenate all of the diolefins, acetylenes and alkenyl aromatics and to maintain an excess of hydrogen at the reactor outlet. In order to limit the temperature gradient in the reactor, it may be advantageous to recycle a fraction of the effluent to the inlet and/or to the centre of the reactor.

EXAMPLES

The following examples illustrate the invention without limiting the scope thereof:

Example 1: Preparation of a Catalyst C1 According to the Invention

This example shows the preparation of a catalyst according to the invention comprising impregnation of the support in two stages according to the process of the invention, that is, by using a colloidal solution for the Pd. The catalyst obtained comprises a fine crust of palladium and silver having a proximity ratio PR on a scale of 0.5 to 2.

A colloidal suspension of Pd oxide is prepared under agitation at 25° C. by diluting 1.8 g of a solution of palladium nitrate $Pd(NO_3)_2$ containing 8.5 wt. % of palladium Pd with approximately 45 ml demineralised water, then adding approximately 10 ml of sodium hydroxide solution to give a pH of 2.4. The suspension is then diluted with demineralised water to a volume which corresponds to the pore volume of the alumina support. This solution is then impregnated onto 80 grams of an alumina having a specific surface area of 71 $m^2/g$, moulded into the form of beads. A maturation step for the impregnated support is carried out before drying in air in a confined moist medium, for a period of 20 h. The solid obtained is dried in air for 2 h at 120° C. The catalyst is then calcined in a stream of air at 450° C. for 2 h.

The solid obtained is immersed in 500 ml of a 1.4 g/l solution of formic acid. The solution is agitated for 2 h at 25° C. The solid is then filtered and washed three times with 500 ml water. The reduced solid is then immersed in 500 ml of a 0.23 g/l solution of silver nitrate at 30° C. for 5 h. The solid obtained is filtered, washed three times with 500 ml water, then dried for 3 h at 120° C. and calcined for 2 h at 570° C.

The catalyst C1 thus prepared contains 0.19 wt. % palladium and 0.10 wt. % silver.

Characterisation of the catalyst C1 by Castaing microprobe reveals that 80% of the Pd is distributed in a crust with a thickness of approximately 80 µm. 80% of the silver is distributed in a crust of approximately 110 µm thickness. The sodium is homogeneously distributed with a distribution coefficient R(Na)=0.92. The apparent dispersion of the palladium of the catalyst C1 is 17%. The proximity factor PR is 1.40.

Example 2: Preparation of a Catalyst C2 According to the Invention

This example is identical to Example 1 with the exception of the palladium concentration, which is half as high as in Example 1. This gives a catalyst with a thinner crust and a better proximity factor PR.

A colloidal suspension of Pd oxide is prepared under agitation at 25° C. by diluting 0.95 g of a solution of palladium nitrate $Pd(NO_3)_2$ containing 8.5 wt. % of palladium Pd with approximately 45 ml demineralised water, then adding approximately 10 ml of sodium hydroxide solution to give a pH of 2.4. The suspension is then diluted with demineralised water to a volume which corresponds to the pore volume of the alumina support. This solution is then impregnated onto 80 grams of an alumina having a specific surface area of 71 $m^2/g$, moulded into the form of beads. A maturation step for the impregnated support is carried out before drying in air in a confined moist medium, for a period of 20 h. The solid obtained is dried in air for 2 h at 120° C. The catalyst is then calcined in a stream of air at 450° C. for 2 h.

The solid obtained is immersed in 400 ml of a 0.87 g/l solution of formic acid. The solution is agitated for 2 h at 25° C. The solid is then filtered and washed three times with 500 ml water. The reduced solid is immersed in 500 ml of a 0.23 g/l solution of silver nitrate at 30° C. for 5 h. The solid obtained is filtered, washed three times with 500 ml water, then dried for 2 h at 120° C. and calcined for 3 h at 570° C.

Catalyst C2 contains 0.1 wt. % palladium and 0.1 wt. % silver.

Characterisation of the catalyst by Castaing microprobe reveals that 80% of the palladium is distributed in a crust with a thickness of approximately 40 µm. 80% of the silver is distributed in a crust of approximately 70 µm thickness. The Na is homogeneously distributed with a distribution coefficient R(Na)=0.93. The apparent dispersion of the palladium is 16%. The proximity factor PR is 1.27.

Example 3: Preparation of a Catalyst C3 Not Conforming to the Invention

This example shows the preparation of a catalyst not conforming to the invention comprising impregnation of the support in two stages according to conventional impregnation methods (that is, without using a colloidal solution for the Pd). The catalyst obtained comprises a relatively thick crust, but having a proximity ratio PR on a scale of 0.5 to 2.

A solution of palladium nitrate is prepared under agitation at 25° C. by diluting 2.7 g of a solution of palladium nitrate Pd(NO$_3$)$_2$ containing 8.5 wt. % of palladium Pd with approximately 50 ml demineralised water. This solution is then impregnated onto 80 g of an alumina having a specific surface area of 71 m$^2$/g, moulded into the form of beads. The solid obtained is dried in air for 2 h at 120° C. The catalyst is then calcined in a stream of air at 450° C. for 2 h.

The solid obtained is immersed in 500 ml of a 2.3 g/l solution of formic acid. The solution is agitated for 2 h at 25° C. The solid is then filtered and washed three times with 500 ml water. The reduced solid is immersed in 500 ml of a 0.4 g/l solution of silver nitrate at 30° C. for 5 h. The solid obtained is filtered, washed three times with 500 ml water. The solid obtained is dried in air for 2 h at 120° C. The catalyst is then calcined in a stream of air at 570° C. for 2 h.

Catalyst C3 contains 0.28 wt. % palladium and 0.17 wt. % silver.

Characterisation of the catalyst by Castaing microprobe reveals that 80% of the palladium is distributed in a crust with a thickness of approximately 200 µm. 80% of the silver is distributed in a crust of approximately 120 µm thickness. The apparent dispersion of the palladium of catalyst C3 is 20%. The proximity factor PR is 0.92.

Example 4: Preparation of a Catalyst C4 Not Conforming to the Invention

This example shows the preparation of a catalyst not conforming to the invention comprising impregnation of the support in two stages according to conventional impregnation methods (that is, without using a colloidal solution for the Pd). The catalyst obtained comprises a relatively thin crust and has a proximity ratio PR outside the scale of 0.5 to 2.

A solution of palladium nitrate is prepared under agitation at 25° C. by diluting 2.7 g of a solution of palladium nitrate Pd(NO$_3$)$_2$ containing 8.5 wt. % of palladium Pd with approximately 50 ml water. This solution is then impregnated onto 80 g of an alumina having a specific surface area of 71 m$^2$/g. The solid obtained is dried in air for 2 h at 120° C. The catalyst is then calcined in a stream of air at 450° C. for 2 h.

A solution of palladium nitrate is prepared under agitation at 25° C. by diluting 0.24 g of a solution of the metal salt in demineralised water in a volume corresponding to the pore volume of the alumina support. The solid obtained is dried in air for 2 h at 120° C. The catalyst is then calcined in a stream of air at 450° C. for 2 h.

Catalyst C4 contains 0.29 wt. % palladium and 0.2 wt. % silver.

Characterisation of the catalyst C4 by Castaing microprobe reveals that 80% of the palladium is distributed in a crust with a thickness of approximately 190 µm. 80% of the silver is distributed in a crust of approximately 40 µm thickness. The apparent dispersion of the palladium of catalyst C4 is 24%. The proximity factor PR is 0.30.

The graphic representation of the ratio PR for the catalysts C1 to C4 is given in FIG. 1. Catalysts C1, C2 and C3 have a PR within the range 0.5 to 2 within the crust, where 80% of the metals Pd and Ag is concentrated. The two metals Pd and Ag are thus locally well associated within the crust. Catalyst C4 has a PR outside the scale as defined.

Example 5: Preparation of a Catalyst C5 Not Conforming to the Invention

This example shows the influence of the specific surface area of the support for a catalyst prepared according to the invention comprising impregnation of the support in two stages according to the process of the invention (that is, by using a colloidal solution for the Pd). The catalyst obtained comprises a relatively thick crust and has a proximity ratio PR within a scale of 0.5 to 2.

A colloidal suspension of Pd oxide is prepared under agitation at 25° C. by diluting 1.8 g of a solution of palladium nitrate Pd(NO$_3$)$_2$ containing 8.5 wt. % of palladium Pd with approximately 45 ml demineralised water, then adding approximately 10 ml of sodium hydroxide solution to give a pH of 2.4. The suspension is then diluted with demineralised water to a volume which corresponds to the pore volume of the alumina support. This solution is then impregnated onto 80 grams of an alumina having a specific surface area of 5 m$^2$/g, moulded into the form of beads. A maturation step for the impregnated support is carried out before drying in air in a confined moist medium, for a period of 20 h. The solid obtained is dried in air for 2 h at 120° C. The catalyst is then calcined in a stream of air at 450° C. for 2 h.

The solid obtained is immersed in 500 ml of a 1.4 g/l solution of formic acid. The solution is agitated for 2 h at 25° C. The solid is then filtered and washed three times with 500 ml water. The reduced solid is immersed in 500 ml of a 0.23 g/l solution of silver nitrate at 30° C. for 5 h. The solid obtained is filtered, washed three times with 500 ml water, then dried for 3 h at 120° C. and calcined for 2 h at 570° C.

Catalyst C5 thus prepared contains 0.17 wt. % palladium and 0.10 wt. % silver.

Characterisation of the catalyst C5 by Castaing microprobe reveals that 80% of the palladium is distributed in a crust with a thickness of approximately 180 µm. 80% of the silver is distributed in a crust of approximately 150 µm thickness. The sodium is homogeneously distributed with a distribution coefficient R(Na)=0.92. The apparent dispersion of the palladium in the catalyst C5 is 24%. The proximity factor PR is 1.10.

Example 6: Use of the Catalysts C1, C2, C3, C4 and C5 for Selective Hydrogenation of the Steam-Cracked C3 Cut A feed comprising 92.47 wt. % propylene, 4.12 wt. % propane, 1.18 wt. % methyl acetylene (MA), 1.63 wt. % propadiene (PD) is treated with the catalysts C1, C2, C3, C4 and C5. Prior to reacting, the catalysts of selective hydrogenation are activated under a stream of hydrogen at 160° C. for 2 h. 25 ml of catalyst is placed in a tubular reactor in mode-up flow. The pressure is maintained at 30 bar and the temperature at 27° C. An hourly space velocity (HSV) of 50 h$^{-1}$ is applied. The molar ratio H$_2$/MPAD varies between 0.5 and 4.5 mol/mol. The composition of the feed and of the effluent is continuously measured at the reactor outlet by gas chromatography. The performances are expressed as [C3$^=$effluent−C3$^=$feed]/[MAPD$_{effluent}$−MAPD$_{feed}$], which represents the selectivity of the catalyst as a function of the residual content of MAPD.

TABLE 1

Selectivity [C3$^-$effluent − C3$^-$feed]/[MAPD$_{effluent}$ − MAPD$_{feed}$] during hydrogenation of a steam-cracked C3 cut for a residual MAPD content of 25 ppm.

| Catalyst | Selectivity | PR |
|----------|-------------|------|
| C1 | 51 | 1.40 |
| C2 | 60 | 1.27 |
| C3 | 30 | 0.92 |
| C4 | 2 | 0.30 |
| C5 | 28 | 1.10 |

Catalysts having a thin palladium/silver crust (<120 microns) and a PR within the range 0.5 to 2, on a support having a specific surface area greater than 65 m$^2$/g, enable an extremely significant improvement in selectivity.

BRIEF DESCRIPTION OF THE DRAWINGS

FIG. 1 Illustrates the graphic representation of the ratio PR for the catalysts C1 to C4.

The invention claimed is:
1. A process for preparing a catalyst comprising a porous support grain on which are deposited palladium and silver, and at least one metal selected from the group consisting of the alkalis and the alkaline earths, the porous support grain comprising at least one refractory oxide selected from the group consisting of silica, alumina and silica-alumina, the specific surface area of the porous support grain being within the range 65 to 150 m$^2$/g, the palladium content of the catalyst within the range 0.05 to 0.6 wt. %, the silver content of the catalyst within the range 0.02 to 3 wt. %, at least 80 wt. % of the palladium being distributed in a crust at the periphery of the support, the thickness of the crust being within the range 10 to 160 µm, at least 80 wt. % of the silver being distributed in a crust at the periphery of the support, the thickness of the crust being within the range 10 to 160 µm, the local content of palladium at each point along the diameter of the grain following the same course as the local content of silver, the sum of the contents of alkali and/or alkaline earth metals being within the range 0.02 to 5 wt. %, said process comprising the following steps:
 a step wherein the palladium is introduced onto the support, referred to as step 1, comprising the following steps:
  a step 1a) wherein, in an apparatus, a colloidal suspension of palladium oxide or palladium hydroxide is prepared in an aqueous phase by mixing an aqueous solution 1 comprising at least one hydroxide selected from the group consisting of alkali hydroxides and alkaline-earth hydroxides and an aqueous solution 2 comprising at least one palladium precursor, the solution 2 then the solution 1 being poured into the apparatus or solutions 1 and 2 being poured simultaneously into the apparatus,
  a step 1b) wherein the colloidal suspension is impregnated onto the porous support grain having a specific surface area within the range 65 to 150 m$^2$/g,
  a step 1c) wherein the impregnated support obtained in step 1b) is matured,
  a step 1d) wherein the catalyst obtained in step 1c) is dried,
  a step 1e) wherein the catalyst obtained in step 1d) is calcined,
 then a step wherein the silver is introduced, referred to as step 2, comprising the following steps:
  a step 2a), wherein the catalyst prepared in accordance with step 1 is reduced by placing it in contact with an aqueous solution comprising at least one liquid phase reducing agent,
  a step 2b), wherein the catalyst obtained in step 2a) is filtered,
  a step 2c), wherein the catalyst prepared in step 2b) is impregnated by placing it in contact, under agitation, with an aqueous solution comprising a silver precursor salt,
  a step 2d), wherein the catalyst obtained in step 2c) is filtered,
  a step 2e), wherein the catalyst obtained in step 2d) is dried,
  a step 2f), wherein the catalyst obtained in step 2e) is calcined at a temperature of 450° C. to 700° C.

2. The process for preparing the catalyst according to claim 1, wherein, in the catalyst, the course of the content of palladium and the content of silver may be expressed by a proximity ratio PR within the range 0.5 to 2, the proximity ratio being defined by the following formula:
Proximity ratio:

$$PR(y) = \frac{Q(y)Pd/Q(r)Pd}{Q(y)Ag/Q(r)Ag}$$

where:
 Q (y) Pd=Sum of the palladium concentrations between the edge of the catalytic grain and a distance y from the edge of the grain (wt. %)
 Q (y) Ag=Sum of the silver concentrations between the edge of the catalytic grain and a distance y from the edge of the grain (wt. %)
 Q (r) Pd=Total palladium content of the catalytic grain (wt. %)
 Q (r) Ag=Total silver content of the catalytic grain (wt. %).

3. The process for preparing the catalyst according to claim 1, wherein, in the catalyst, the alkali and/or alkaline-earth metal is homogeneously distributed through the support grain with a coefficient R within the range 0.8 to 1.2, the coefficient R being defined by the following formula:

$$R = \int_{-r}^{r} c(x)x^2\,dx \bigg/ \frac{r^2}{3}\int_{-r}^{r} c(x)\,dx$$

where the distribution profile c(x) for x∈[−r; +r] is obtained with a Castaing microprobe, c being the local concentration locale of the alkali and/or alkaline-earth element, r the radius of the grain, and x the position of the analysis point along the diameter of the grain relative to the centre of this grain.

4. The process for preparing the catalyst according to claim 1, wherein, in the catalyst, the porous support grain is alumina.

5. The process for preparing the catalyst according to claim 1, wherein, in the catalyst, the porous support grain is in the form of beads or extrudates.

6. The process for preparing the catalyst according to claim 1, wherein, in the catalyst, the alkali metal is sodium.

7. The process for preparing the catalyst according to claim 1, wherein the content of palladium in the catalyst is within the range 0.05 to 0.4 wt. %, the silver content of the catalyst is within the range 0.05 to 0.3 wt. %, at least 80 wt. % of the palladium is distributed within a crust at the periphery of the support, the thickness of the crust is within the range 10 to 110 μm, at least 80 wt. % of the silver is distributed within a crust at the periphery of the support, and the thickness of the crust is within the range 10 to 110 μm.

8. A process for preparing the catalyst according to claim 1, wherein, in step 1a), the palladium precursor is selected from the group consisting of palladium chloride, palladium nitrate, and palladium sulphate.

9. A process for preparing the catalyst according to claim 1, wherein, in step 2c), the silver precursor is selected from the group consisting of silver nitrate, silver acetate, silver citrate, silver chloride, and silver oxalate.

10. A process for preparing the catalyst according to claim 1, wherein, in step 2a), the reducing agent is selected from formic acid, citric acid, ascorbic acid, oxalic acid, sodium formiate, sodium acetate, sodium borohydride, formaldehyde, dextrose, hydrazine and hydrogen.

11. The process for preparing the catalyst according to claim 1, wherein the catalyst comprises a porous support grain on which are deposited palladium and silver, and at least one metal selected from the group consisting of the alkalis and the alkaline earths, the porous support grain comprising at least one refractory oxide selected from the group consisting of silica, alumina and silica-alumina, the specific surface area of the porous support being grain within the range 65 to 150 $m^2/g$, the palladium content of the catalyst within the range 0.05 to 0.4 wt. %, the silver content of the catalyst within the range 0.05 to 0.3 wt. %, at least 80 wt. % of the palladium being distributed in a crust at the periphery of the support, the thickness of the crust being within the range 10 to 110 μm, at least 80 wt. % of the silver being distributed in a crust at the periphery of the support, the thickness of the crust being within the range 10 to 110 μm, the local content of palladium at each point along the diameter of the grain following the same course as the local content of silver, the sum of the contents of alkali and/or alkaline earth metals being within the range 0.02 to 5 wt. %, the density of palladium particles within the crust, denoted De, is in the range of 1500 to 4100 particles of palladium per $μm^2$, and the apparent dispersion of the palladium is 5 to 17%.

* * * * *